United States Patent [19]

Carus et al.

[11] Patent Number: 4,753,230
[45] Date of Patent: Jun. 28, 1988

[54] WOUND DRESSING

[75] Inventors: Edmund H. Carus, Darwen; Brian Tomkinson, Rochdale; Edmund King, Bolton, all of United Kingdom

[73] Assignee: J. R. Crompton P.L.C., Lancashire, England

[21] Appl. No.: 768,614

[22] Filed: Aug. 23, 1985

[30] Foreign Application Priority Data

Jun. 12, 1985 [GB] United Kingdom ............... 8514892

[51] Int. Cl.$^4$ ............................................. A61L 15/00
[52] U.S. Cl. ..................................... 128/156; 128/155
[58] Field of Search ................................ 128/156, 155

[56] References Cited

U.S. PATENT DOCUMENTS

| 3,901,240 | 8/1975 | Hoey | 128/156 |
| 4,181,127 | 1/1980 | Linsky et al. | 128/155 |
| 4,240,416 | 12/1980 | Boich | 128/156 |
| 4,510,197 | 4/1985 | Shah | 128/155 |

FOREIGN PATENT DOCUMENTS

| 678354 | 1/1964 | Canada | 128/156 |
| 147119 | 7/1985 | European Pat. Off. | 128/156 |
| 893874 | 4/1962 | United Kingdom | 128/156 |
| 950207 | 2/1964 | United Kingdom | 128/156 |
| 960427 | 6/1964 | United Kingdom | 128/156 |
| 1292133 | 10/1972 | United Kingdom | 128/156 |

Primary Examiner—E. Rollins Cross
Attorney, Agent, or Firm—Handal & Morofsky

[57] ABSTRACT

A wound dressing comprises an absorbent material and a surface layer of a non-absorbent wet laid apertured fabric having a smooth substantially planar surface. The non-absorbent apertured fabric preferably serves to present a soft smooth surface to the wound, maximizing conformability to the wound and minimizing any possibility of adherence of the dressing to the latter. Absorption of exudate from the wound by the absorbent material takes place largely through the apertures in the fabric. The fabric is preferably rendered non-absorbent by a coating of an acrylic latex.

18 Claims, 1 Drawing Sheet

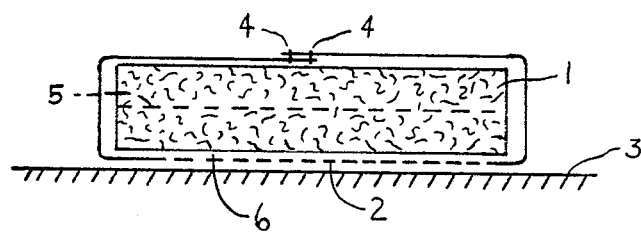

WOUND DRESSING

BACKGROUND OF THE INVENTION

This invention relates to a bandage, pad, swab or other wound dressing.

DISCLOSURE OF THE INVENTION

According to the present invention a wound dressing comprises an absorbent material and a surface layer of non-absorbent wet-laid apertured fabric having a smooth substantially planar surface, the surface layer being saturation coated with a polymer derived from an alkyl acrylate. Absorption of exudate from the wound by the absorbent material takes place largely through the more open apertures in the fabric.

The smooth surface of the dressing minimises disruption of the healing of the wound due to friction between wound and dressing. Any movement with abrasive dressings impedes migration of epithelial cells. The hydrophobic coating of the acrylate polymer reduces adhesion of the dressing to the wound by ensuring as far as possible neither loose fibres nor unbonded fibres at the fibre cross-over points lint or protrude into the wound to interfere with epithelialisation. Saturation coating of the entire surface layer is preferred to optimise the non-adherence of the dressing.

The polymer used for coating may be a polymer derived solely from an alkyl acrylate, for example ethyl acrylate or more preferably butyl acrylate. Coatings may comprise co-polymers of an alkyl acrylate and one or more additional monomers, for example: acrylic acid, acrylonitrile, N-methylolacrylamide or styrene. Preferred co-polymers are derived from not less than 90% $^w/w$ of alkyl acrylate, preferably butyl acrylate.

It is important that the coating does not stiffen the dressing, softness being important to ensure the dressing conforms to the wound and to minimise abrasion.

A cellulosic apertured fabric is preferred, rayon being especially preferred.

The wet-laid fabric may be apertured according to the process disclosed in United Kingdom Patent Specification No. 836397 wherein a web is apertured by the passage of jets of water.

The ratio of the length to cross directionality of the fibres in the web is preferably less than 5.5 more preferably within the range 2.5 to 4.5. This is important because the apertures in the web are produced by washing of fibres away from corresponding apertures in an overlying screen. The fibres tend to be washed laterally. Use of a web having a high ratio of length to cross directionality produces eliptical apertures, causing the resultant fabric to have ridges in the lengthwise direction. A more planar surface is produced if a low ratio is employed. Such a fabric has the additional advantage of strength in both length and cross directions, facilitating sewing, for example into swabs.

Any suitable absorbent fibrous or other material including fluff pulp may be used for filling the dressing although absorbent cotton is preferred for the majority of applications. The absorbent material is preferably arranged to lie in direct intimate contact with the inner surface of the fabric over the entire area which may contact a wound. Furthermore, the dressing is preferably constructed so that the absorbent material remains in contact with the fabric after the dressing has been sterilised to provide points of ingress for wound exudate.

A layer of wadding, paper or other liquid conducting material may be inserted or otherwise disposed between the fabric and absorbent material or between layers of the absorbent material to ensure efficient and even transport of liquid within the dressing.

The invention is further described by means of example and not in any limitative sense, with reference to the accompanying drawing which illustrates an example thereof.

DETAILED DESCRIPTION

The drawing illustrates a wound dressing in accordance with this invention. A body of absorbent material such as absorbent cotton 1 is disposed in contact with a surface layer of non-absorbent apertured fabric 2 which in use is placed in contact with the wound 3 and joined at the back of the dressing by suitable adhesive means 4. The absorbent material serves to absorb exudate from the wound. Absorbent cotton having a weight of 10 to 500 $gm^{-2}$ is preferred more preferably 150 $gm^{-2}$, this having a good absorbency combined with conformability. Alternative absorbent materials include absorbent fibres, viscose products and modified viscose products e.g. Courtaulds SI or VILOFT or comminuted wood pulp products such as fluff pulp.

It is strongly preferred that the material 1 is in contact with the fabric 2 over the entire area where the fabric contacts the wound. A layer of paper, wadding or other absorbent material may be disposed within the dressing, for example within the material 1 to improve the distribution of liquid within the dressing.

The outer surface of the dressing is smooth to minimise adherence to and abrasion of the wound and to assist conformability. The fabric is rendered non-absorbent by a hydrophobic coating derived from an alkyl acrylate. A coating of a cross linked copolymer derived from 90% $^w/w$ of butyl acrylate together with small amounts of acrylic acid, acrylonitrile and N-methylolacrylamide has been found to be particularly suitable. A complete uniform coating is preferably applied to the fabric by saturation coating, applying between 5 and 45% latex solids on dry fibre, preferably between 15 and 35%, and more preferably 25% latex solids, for example by means of a paper making size press. Spraying, foaming or other means of application may be employed.

A wet laid fabric suitable for use in manufacture of dressings in accordance with this invention may be apertured in accordance with the disclosure of the United Kingdom Patent Specification No. 836397. According to this disclosure a non-woven web is apertured by passage of jets of water through apertures in a screen in the vicinity of which the underlying web is supported on a porous fabric. The size and shape of the apertures is dependent on several factors including the size and arrangement of the apertures in the screen, and just as importantly, the pitch of adjacent holes in the screen, the pressure of the water and the nature of the web. To achieve this the dressing cover typically incorporates four apertures per centimetre in the length direction of the fabric and four to five apertures per centimetre in the cross direction of a generally circular appearance of approximately 2 mm diameter with some bridging of apertures by fibres, e.g. arranged in a square or diagonal array. The ratio of the length to cross directionality of the fibres of the web is important to the shape of the apertures formed. A ratio of less than 5.5 is preferred, a ratio of 2.5 to 4.5 being especially preferred, since high ratios tend to produce eliptical apertures causing ridges in the resultant fabric. A low ratio enhances the strength of the fabric and hence the ease of sewing of the dressing, for example for manufacture of swabs.

The fabric may be composed of polyester, polypropylene, polyamide or other manmade fibres. Rayon is especially preferred on account of the flexibility and lack of resilience which facilitates the aperturing process and allows for good conformability of the dressing to the wound. A range of fibre deniers may be used but preferably a fabric composed of 1.5 denier Rayon fibres. A fibre length of 5 to 20 mm may be used, preferably between 7 and 13 mm, and more preferably 10 mm at 1.5 denier. Fibres of mixed lengths and of mixed deniers may also be employed but generally without exceeding the fibre length to diameter ratios indicated.

The weight of the dressing cover in accordance with this invention is important. A preferred cover fabric has a weight of 9 to 19 $gm^{-2}$, preferably 11 to 17 $gm^{-2}$, more preferably 14 $gm^{-2}$.

Dressings in accordance with this invention may take many forms. A sleeve of fabric may be suitably disposed around a pad of the absorbent material. A multiple ply absorbent dressing such as a filamated swab may be provided alternatively.

The interface 5 between such multiple plies is illustrated in the figure. In addition, a layer of liquid conducting material may be positioned at interface 5 in the space 6 and between fabric 2 or material 1 as illustrated in the FIGURE. A sewn dressing, such as a laparotomy swab has an important advantage that migration of fibres of the absorbent material to the body cavity is impeded by the hydrophobic saturation coating.

The invention is further described by means of an example.

EXAMPLE

An apertured fabric having a weight of 14 $gm^{-2}$ was prepared from a wet laid web which contained a suitable bonding agent such as highly hydrated or fibrillated cellulose floc. The web was apertured in accordance with the process disclosed in United Kingdom Patent Specification No. 836397. The resultant web was bonded using heat prior to saturation with a butyl acrylate copolymer latex e.g. Acronal A35D (BASF) by passage through a papermaking size press nip to give 25% latex solids added to dry fibre. The resultant apertured non-absorbent fabric was placed in contact with a pad of absorbent cotton BP having a weight of 150 $gm^{-2}$ produced by superimposition of carded fleeces. The pad was enveloped with the fabric and the latter was secured by an adhesive thread to produce a wound dressing.

Dressings prepared as described above were assessed on standard partial thickness wounds of 2.5 $cm^2$ on the Domestic Pig. The method used is described in "Medical Applications of Textiles" S. J. Varley, S. Barnett and J. T. Scales, Symposium Proceedings published by Leeds University 1981. The skin structure and healing reactions of the pig closely resemble those of humans. Epithelialisation or skin regeneration of the wounds after three days was 100% with the dressings in situ. 85% regeneration was observed with most proprietory wound dressings and only 75% regeneration was exhibited by use of surgical gauze, BP Type 13, Light.

What we claim is:

1. A wound dressing comprising an absorbent material and a surface layer of a non-absorbent, wet-laid apertured fabric having a smooth substantially planar surface wherein the ratio of length to cross directionality of the fibres of the fabric is less than 5.5, the surface layer being coated with a polymer derived from an alkyl acrylate.

2. A dressing as claimed in claim 1, wherein the polymer is derived from butyl acrylate.

3. A dressing as claimed in claim 2, wherein the polymer comprises a co-polymer of small amounts of acrylic acid, acrylonitrile and N-methylolacrylamide and not less than 90% w/w butyl acrylate.

4. A dressing as claimed in claim 1, wherein said ratio lies within the range 2.5 to 4.5.

5. A dressing as claimed in claim 1, wherein the absorbent material is arranged is direct intimate contact with the inner surface of the fabric over the entire area which may contact a wound.

6. A dressing as claimed in claim 1, wherein a layer of liquid conducting material is disposed between the fabric and absorbent material.

7. A dressing as claimed in claim 1, wherein there are two or more layers of absorbent material, a layer of liquid conducting material being disposed between said layers of the absorbent material.

8. A dressing as claimed in claim 1, wherein the absorbent material comprises cotton having a weight of 10 to 500 $gm^{-2}$.

9. A dressing as claimed in claim 8, wherein the absorbent cotton has a weight of 150 $gm^{-2}$.

10. A dressing as claimed in claim 1, wherein the coating of polymer is applied by saturation coating.

11. A dressing as claimed in claim 1, wherein the fabric comprises rayon.

12. A dressing as claimed in claim 1, wherein the fabric comprises fibres predominantly of not greater than 6 denier.

13. A dressing as claimed in claim 12, wherein the fibres are of 1.5 denier.

14. A dressing as claimed in claim 1, wherein the fabric comprises fibres with lengths of 5 to 20 mm.

15. A dressing as claimed in claim 14, wherein the fabric comprises 1.5 denier fibres with a length of 10 mm.

16. A dressing as claimed in any preceding claim wherein the fabric has a weight of 9 to 19 $gm^{-2}$.

17. A dressing as claimed in claim 16, wherein the fabric has a weight of 11 to 17 $gm^{-2}$.

18. A dressing as claimed in claim 17, wherein the fabric has a weight of 14 $gm^{-2}$.

* * * * *